(12) United States Patent
Eckstein et al.

(10) Patent No.: US 8,771,244 B2
(45) Date of Patent: *Jul. 8, 2014

(54) ATTACHMENT DEVICE FOR USE IN THE VACUUM THERAPY OF WOUNDS

(75) Inventors: Axel Eckstein, Heidenheim (DE); Juergen Hofstetter, Heidenheim (DE); Pierre Croizat, Herbrechtingen (DE); Klaus Klimenta, Osterwieck OT Zilly (DE); Steffen Suess, Halberstadt (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 191 days.

This patent is subject to a terminal disclaimer.

(21) Appl. No.: 12/974,067

(22) Filed: Dec. 21, 2010

(65) Prior Publication Data

US 2011/0152800 A1 Jun. 23, 2011

Related U.S. Application Data

(60) Provisional application No. 61/295,180, filed on Jan. 15, 2010.

(30) Foreign Application Priority Data

Dec. 23, 2009 (DE) .......................... 10 2009 060 596

(51) Int. Cl.
*A61M 1/00* (2006.01)
*A61M 27/00* (2006.01)
(52) U.S. Cl.
USPC ............................ 604/315; 604/313; 604/543

(58) Field of Classification Search
USPC ......... 604/180, 307, 313–316, 540, 541, 543; 602/42, 46, 47, 52–54
See application file for complete search history.

(56) References Cited

U.S. PATENT DOCUMENTS

| 5,116,310 | A | * | 5/1992 | Seder et al. | 604/43 |
| 6,626,891 | B2 | * | 9/2003 | Ohmstede | 604/543 |
| 7,198,046 | B1 | | 4/2007 | Argenta | |
| 8,083,712 | B2 | * | 12/2011 | Biggie et al. | 604/73 |
| 2006/0229586 | A1 | * | 10/2006 | Faries, Jr. | 604/506 |
| 2008/0108977 | A1 | * | 5/2008 | Heaton et al. | 604/543 |
| 2008/0271804 | A1 | * | 11/2008 | Biggie et al. | 138/137 |
| 2009/0227968 | A1 | | 9/2009 | Vess | |

(Continued)

FOREIGN PATENT DOCUMENTS

| DE | 10 2005 015 878 | 10/2006 |
| DE | 10 2008 020 553 | 10/2008 |

(Continued)

*Primary Examiner* — Tan-Uyen T Ho
*Assistant Examiner* — Mark K Han
(74) *Attorney, Agent, or Firm* — Paul Vincent

(57) ABSTRACT

An attachment device (2) for use in the vacuum therapy of wounds has a vacuum-tight mounting element (6). A conduit is fastening to the upper side of that mounting element in a vacuum-tight manner. The conduit (4) communicates with the wound space through openings (22) in the mounting element (6) and in the vacuum dressing. The conduit (4) is flexible and flat and is connected to the mounting element (6) non-detachably and extensively in a longitudinal section (8) on the wound side over at least 70% of its surface projected perpendicularly onto the mounting means (6). The conduit (4) is made out of a flexible elastomer material of Shore A hardness of no more than 60 and the thickness (D) of the combined conduit (4) and mounting element (6) is no more than 7 mm.

15 Claims, 4 Drawing Sheets

(56) References Cited

U.S. PATENT DOCUMENTS

2009/0234307 A1  9/2009 Vitaris
2009/0281526 A1  11/2009 Kenny
2010/0160901 A1* 6/2010 Hu et al. .................. 604/543
2010/0324510 A1* 12/2010 Andresen et al. ........... 604/319
2012/0116334 A1* 5/2012 Albert et al. ............... 604/319
2013/0066284 A1* 3/2013 Croizat et al. ............. 604/313

FOREIGN PATENT DOCUMENTS

| DE | 20 2009 005 934 | 7/2009 |
| DE | 20 2009 016 804 | 4/2010 |
| EP | 2 098 257 | 9/2009 |
| WO | WO 03/057307 | 7/2003 |
| WO | WO 2009/002260 | 12/2008 |

* cited by examiner

ATTACHMENT DEVICE FOR USE IN THE VACUUM THERAPY OF WOUNDS

This application claims benefit of U.S. 61/295,180 filed Jan. 15, 2010 as well as Paris convention priority of DE 10 2009 060 596 filed Dec. 23, 2009, the entire disclosures of which are hereby incorporated by reference.

BACKGROUND OF THE INVENTION

The invention relates to an attachment device for use in the vacuum therapy of wounds, with a conduit to which a vacuum can be applied, with a large-surface vacuum-tight mounting means, to whose topside, facing away from the wound, the conduit is vacuum-tightly fastened, wherein the mounting means can be attached to a vacuum dressing covering and tightly sealing the wound against the atmosphere, preferably using an additional adhesive film, wherein the conduit communicates with the wound space through openings in the mounting means and in the vacuum dressing.

The importance of the vacuum therapy of wounds, in particular, of wounds that are deep and whose healing is therefore problematic, has recently grown. Vacuum therapy means that a region of the body or wound that would otherwise be exposed to the atmosphere is pressure-tightly and vacuum-tightly sealed against the environment, that is, the atmosphere in which we live and breathe, by means to be described in more detail below, wherein a pressure that is reduced with respect to atmospheric pressure in a manner still be described, which is therefore negative pressure with respect to the atmosphere, can be applied and continuously maintained within the sealed wound space. Where mention is made herein of a vacuum on the region, this refers to a pressure range of typically between 0 and 500 mm Hg (mm of mercury) below the ambient atmospheric pressure. It has been shown that this is conducive to wound healing. Vacuum-tight sealing can be achieved with a vacuum dressing that, for example, can comprise a pressure-tight or vacuum-tight film layer, which is typically adhesively bonded to an intact region of the body surrounding the wound, thus providing a tight seal. To supply vacuum into the wound space and maintain it there, from a device for producing a vacuum, that is, a vacuum pump in the broadest sense, in the case of the systems stated here for the vacuum therapy of wounds, conduits can be used to which a vacuum is applied that act in conjunction with the vacuum dressing by means of an attachment device to apply a vacuum on or in the wound space. Such an attachment device of the type stated in the introduction is known, for example, from WO 2006/052338 A2. Circular-section tubes are used to supply the vacuum to the wound.

The object of this invention is to provide an attachment device of the type stated in the introduction, which proves pleasant or hardly painful for the patient on application or contact and wherein the sealing of the components can be achieved with a technically and economically reasonable effort and in a user-friendly manner.

SUMMARY OF THE INVENTION

This object is inventively solved with an attachment device of the stated type by constituting the conduit to be flexible and flat and connecting it to the mounting means for the intended use non-detachably and extensively in a longitudinal section on the wound side over at least 70% of its surface projected perpendicularly onto the mounting means and by making the conduit from a flexible elastomer material of Shore A hardness of no more than 60 (determined according to DIN 53505 dated August 2000), wherein the thickness of the combined conduit and mounting means is no more than 7 mm, in particular, no more than 6 mm, and further, in particular, no more than 5 mm.

The conduit is therefore not tubular with an essentially circular cross-section but has a flat shape whose width is much larger than its thickness. In conjunction with the choice of materials, this results in a flexible conduit that proves more pleasant for the patient when contact pressure is exerted on the attachment device or the conduit. This results in less concentrated loading that could cause pain and that is very problematical, in particular, in the case of fresh pain-sensitive wounds. Moreover, due to the flat shape, there is less danger of becoming hooked or caught. Because, in that longitudinal section with which it is fastened to the carrier, the conduit is extensively connected to the large-area mounting means over at least 70% of its surface projected perpendicularly onto the mounting means (including the opening or openings in the wall of the conduit), a pressure load is spread over a larger area of the wound dressing, which proves very advantageous in respect of the problems stated above. The conduit, in the longitudinal section used for fixture, is preferably connected to the mounting means over at least 80%, in particular, over at least 90% and further in particular over at least 95% of its surface projected perpendicularly onto the mounting means.

The above-mentioned width of the flat conduit is at least 10 mm, in particular, at least 15 mm and further, in particular, at least 18 mm and in particular, no more than 30 mm and further, in particular, no more than 25 mm.

The elastomer material from which the conduit is made preferably has a Shore A hardness of 5 to 60, in particular, of 10 to 60, in particular, of 15 to 50, in particular, of 15 to 40 and further in particular, of 15 to 35. As already stated, the Shore A hardness is determined according to DIN 53505 dated August 2000 and at 23° C. on a plate-shaped flat and smooth specimen of thickness 6 mm as described in the standard. According to a preferred embodiment of the invention, the conduit is made of a silicone-based material.

Because the flat and flexible conduit is used to supply a vacuum into the wound space and possibly to supply rinsing liquids or rinsing gases and to remove wound exudates, that is, preferably merely has a duct-forming communication function, it is proposed that the conduit not be constituted in a laminar fashion with multiple components or layers but, despite its flat shape, tubular, that is, seen in cross-section in the circumferential direction, completely as one integral element made of one material.

Further, it proves advantageous if the conduit has means inside to prevent collapse of the conduit when a vacuum is applied that are integrally molded, in particular, forming one integral element with the material of the conduit. These means to prevent collapse of the conduit are especially suitable in the case of a tubular conduit as described above. These means to prevent collapse can, for example, be formed from ribs or protrusions. In a further embodiment of this inventive idea, it proves advantageous if they extend from end to end. The conduit can then be advantageously constituted as an extruded part.

It can further prove advantageous if the conduit comprises multiple ducts pressure-tightly separated from each other, wherein the conduit is preferably constituted as one integral element even in such a case, that is, does not comprise a combination of multiple separate duct-forming means. The multiple ducts can comprise a rinsing duct that can supply a rinsing medium toward the end of the attachment device facing the wound and a vacuum duct that is used to supply the vacuum or to remove wound exudates. In this manner, any blockages in the conduit can be freed. Each duct communicates with at least one opening in the conduit.

The flat conduit preferably extends over a certain distance in the longitudinal direction and can then make a transition to a usual torsionally rigid round tube through a non-depicted transition or coupling element that can form a plug connection or adhesive connection that leads to a device producing a vacuum which, in turn, can be constituted as a stationary device or as a mobile device that can be carried on the body of the patient. The transition or coupling element can also be capable of coupling a multiple-duct conduit to a multiple-duct round tube. A distance of 10 to 60 cm has proven the convenient length of the flat conduit.

The large-area mounting means of the attachment device with which the flat conduit is vacuum-tightly connected by the manufacturer is preferably also made of a flexible elastomer material with a Shore A hardness of 5 to 60, in particular, of 10 to 60, in particular, of 15 to 50, in particular, of 15 to 40 and further, in particular, of 15 to 35. The large-area mounting means advantageously has a thickness of 0.75 to 3 mm, in particular, of 1 to 3 mm. According to a preferred embodiment of the invention, it is made of a silicone-based material. According to a further preferred embodiment, the conduit and the mounting means are made of the same elastomer material. The mounting means is used to hold the flat conduit in a longitudinal end section communicating with the wound space and support it evenly. Its area is therefore larger than the area of the conduit in said longitudinal end section at the wound end. It proves advantageous if the area of the mounting means is at least 1.5 times and preferably at least twice the area of the conduit projected perpendicularly onto the mounting means because, in this way, the forces introduced through the conduit on contact are distributed over a larger area and also flexural torques that are exerted on the conduit are not transmitted or only transmitted to a lesser degree to the vacuum dressing; they are better absorbed by the plate-shaped mounting means. It proves sufficient if the area ratio stated above is no more than 5, in particular, no more than 4, wherein a ratio from 2 to 3 has proven advantageous.

The flat conduit could, for example, have a rectangular shape when viewed in cross-section, wherein the two narrow sides can preferably also be rounded. According to a further embodiment of the invention, the conduit is constituted trapezoidal when viewed in cross-section. The narrow sides then slant with an angle of inclination with respect to the plane of the wide-area mounting means of, for example, 25° to 60°, in particular, 35° to 50°, wherein the edges of the one-sided or preferably two-sided trapezoidal shape does not have to be straight but can also be rounded.

Vacuum-tight connection of the flat conduit with the topside of the mounting means facing away from the wound is essential for correct functioning. For this purpose, an adhesive connection using an adhesion promoter in the broadest sense must necessarily be used. A thermal joint also proves advantageous, which can be a kind of vulcanized joint. For example, the conduit previously manufactured separately can be applied to the freshly cast and only partially cured large-area mounting means to achieve a materially bonded close connection of the two components without the use of an additional adhesion promoter.

It proves advantageous if the intercommunicating openings in the conduit and in the mounting means coincide with each other, that is, are aligned with each other. This proves to be most simply manufactured if these openings are formed at the same time in both components only after vacuum-tight connection of the flat conduit to the large-area mounting means. This can be achieved, for example, using a material-removing punching process.

With respect to the number and the size of the openings in the conduit and in the large-area mounting means it would be conceivable for only a single opening to be provided. However, it proves advantageous if, in the vacuum-tight connection region of the conduit and mounting means, multiple openings, in particular, at least two, in particular, at least four openings per cm length of the conduit are provided.

It also proves advantageous if the clearance opening area of the openings is 5 to 50% of the area of the non-detachably joined flat sides of the conduit and mounting means.

The inventive attachment device therefore comprises, as its main components, the flat and flexible conduit and the large-area mounting means that holds and evenly supports the conduit. Further adhesion promoters are then required to connect the whole attachment device vacuum-tightly to the vacuum dressing that seals the wound to be treated tightly against the atmosphere, preferably detachably. For example, it would be conceivable for an adhesive sealing element, for example, an adhesive coating or adhesive film, to be provided on the underside of the large-area mounting means facing the vacuum dressing. According to a further inventive idea, it proves advantageous if the mounting means can be attached to the vacuum dressing using an additional adhesive film, wherein the additional adhesive film is provided on the side of the large-area mounting means facing away from the wound and overlaps the mounting means along its edge/perimeter but preferably omits the conduit, that is, does not cover it. Because the conduit is not covered, no folds are formed in the adhesive film that would be problematical both visually and functionally with respect to the sealing function. With the region of the adhesive film overlapping the entire perimeter of the mounting means in the circumferential direction, the attachment device can then be fastened vacuum-tightly to the outer side of the vacuum dressing facing away from the wound.

This region of the adhesive film overlapping the perimeter is preferably covered by a strip-off layer that preserves, supports, and protects the adhesive layer before use of the attachment device.

In a further embodiment of the invention, a supporting effect can also be provided by stabilizing the mounting means or the adhesive film overlapping the mounting means at the perimeter with an additional frame-forming support means. This frame-forming support means is then advantageously provided on the side of the mounting means or the adhesive film facing away from the wound. If it is provided on the adhesive film, it is preferably provided outside the mounting means. It can be constituted for permanent attachment to the attachment device or for intended detachment after application of the attachment device to the vacuum dressing.

All the characteristics stated above can be essential to the invention, singly or in any mutual combination with further characteristics. Further characteristics, details, and advantages can be derived from the appended claims and from the drawings and the following description of a preferred embodiment of the invention.

The figures show:

DESCRIPTION OF THE PREFERRED EMBODIMENT

Figure 1:
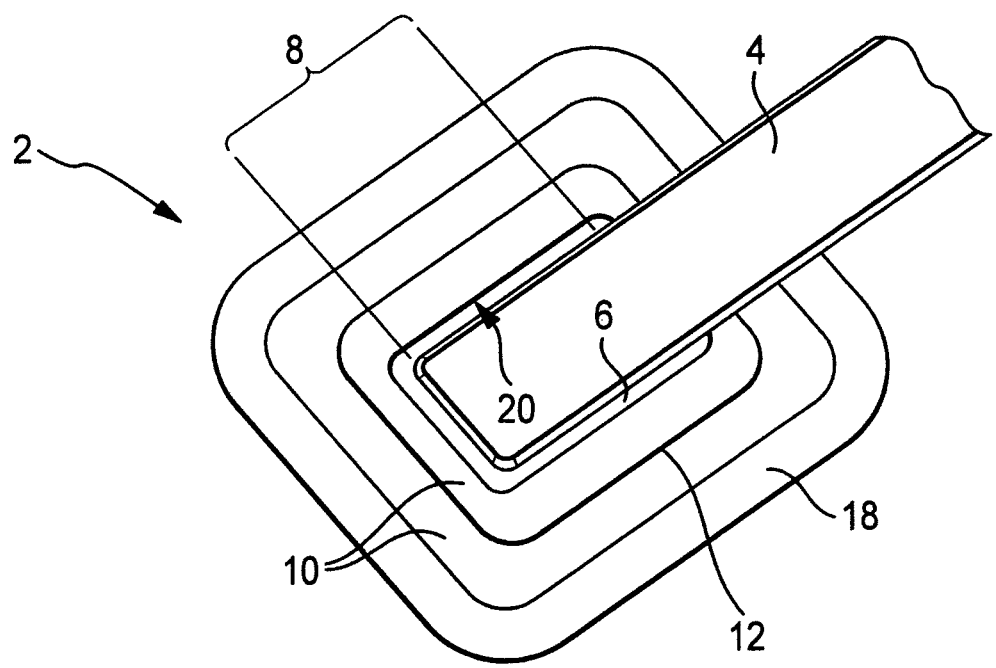
FIG. 1 a perspective view of an inventive attachment device for use in the vacuum therapy of wounds.
Figure 2:
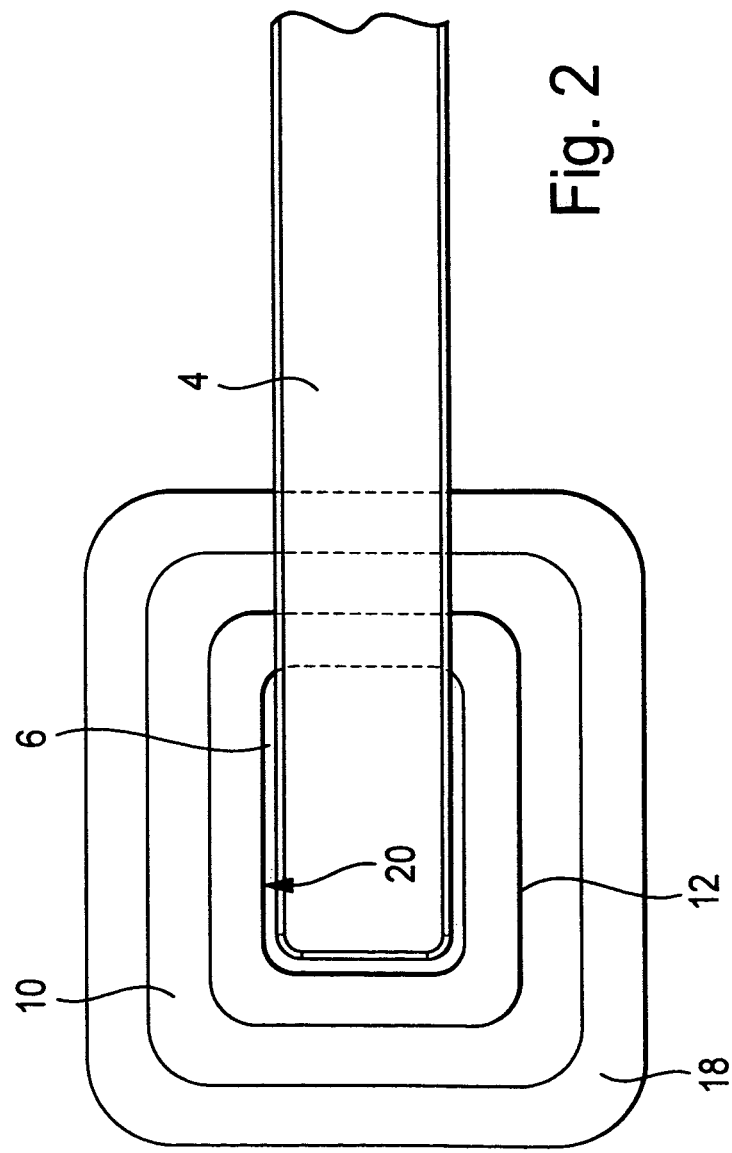
FIG. 2 a plan view of the attachment device according to FIG. 1.
Figure 3:
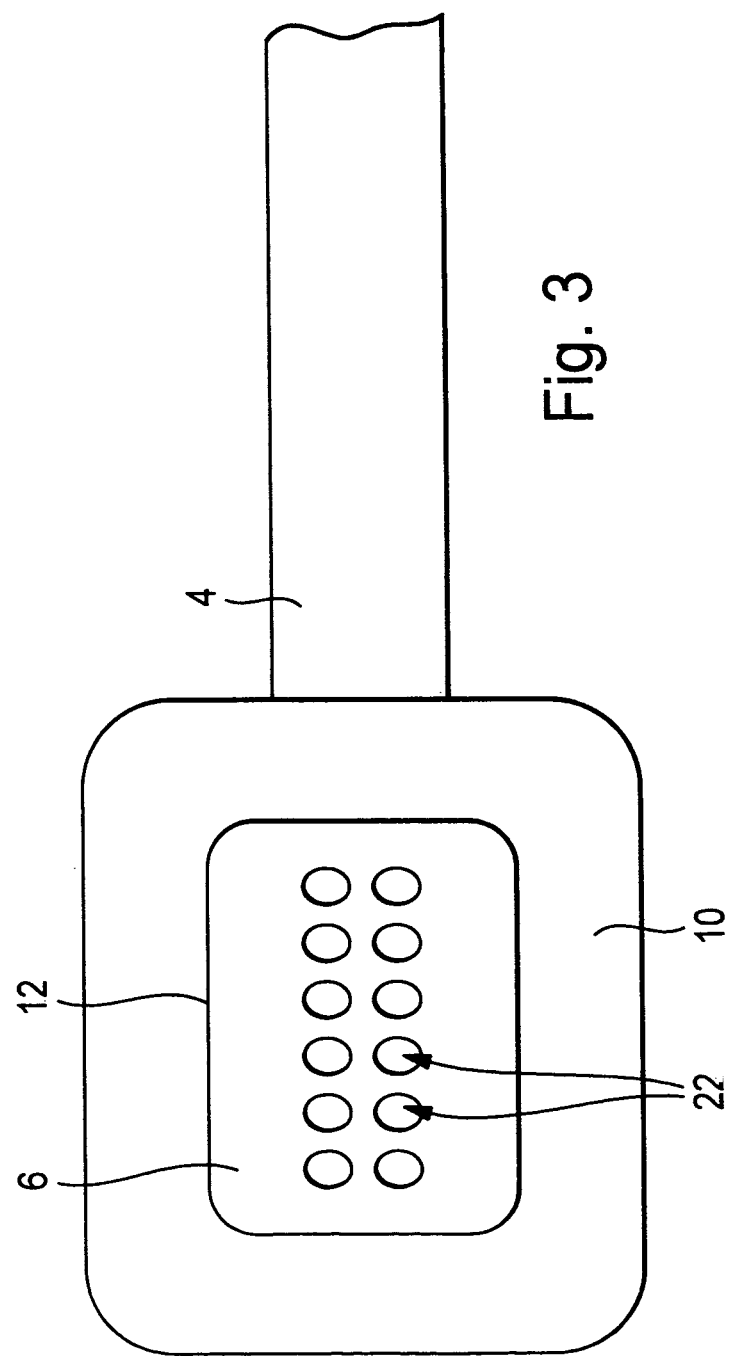
FIG. 3 a view of the attachment device according to FIG. 1 from below (protective film detached)
Figure 4:
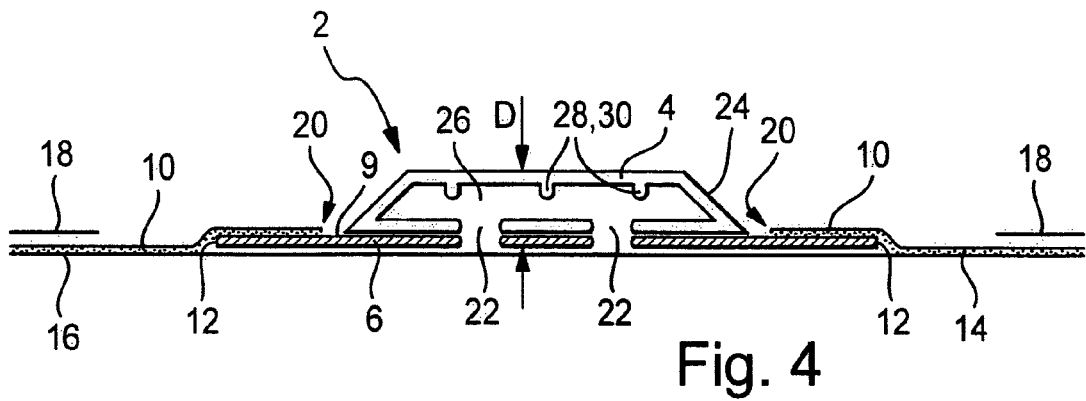
FIG. 4 a schematic view of a non-scale sectional view of the attachment device according to FIG. 1.

FIGS. 1 to 4 show various views of an inventive attachment device collectively designated by the reference symbol 2 for use in the vacuum therapy of wounds. The attachment device 2 is preferably detachably applied to a topside facing way from the wound of a non-depicted vacuum dressing that covers a wound to be treated and seals it vacuum-tightly toward the atmosphere. The attachment device 2 comprises a flat conduit 4 made of an elastomer flexible material and a large-area mounting means 6 that holds and supports the flat conduit 4 so that compressive or flexural forces applied to the conduit 4 can be evenly introduced into and absorbed by the mounting means 6.

The conduit 4 has a flat shape such that it is connected to the mounting means 6 in its longitudinal section 8 with almost 100% of its area projected perpendicularly onto the mounting means 6. The relevant flat side of the conduit 4 can be adhesively bonded or vulcanized, that is thermally joined, onto the topside 9 of the mounting means 6 facing away from the wound.

The large-area plate-shaped mounting means 6 is overlapped around its full circumference by an adhesive film 10 that protrudes outwardly in the circumferential direction, continuously over a circumferential edge 12 of the mounting means 6. The adhesive film 10 bears an adhesive coating 14, by means of which the entire attachment device 2 can be applied vacuum-tightly, but preferably detachably, to the outer side of a non-depicted vacuum dressing facing away from the wound. The region of the adhesive film 10 overlapping the circumferential edge 12 of the mounting means 6 is covered by a removable protective film 16 from below. On the opposite topside of the adhesive film 10, a radially outer frame-forming support means 18 is provided. The adhesive film 10 has an inner gap 20 in that region in which the conduit 4 is connected to the mounting means 6, that is, in the region of the longitudinal section 8 of the conduit 4. If technically feasible, the adhesive film 10 can also overlap the entire mounting means 6, so that it extends between the conduit 4 and the mounting means 6 and is included in the joint between the conduit 4 and mounting means 6.

Preferably after vacuum-tight joining of the conduit 4 to the mounting means 6, the openings 22 are constituted through the mounting means 6 and the conduit 4 that communicate with the non-depicted openings in the vacuum dressing when the attachment device 2 is mounted on the vacuum dressing to apply a vacuum to the wound space.

Figure 5A:
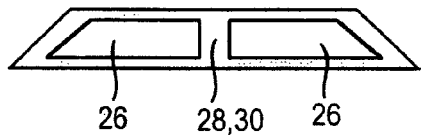
FIGS. 5a, b sectional views of further embodiments of conduits of the inventive attachment device.
Figure 5B:
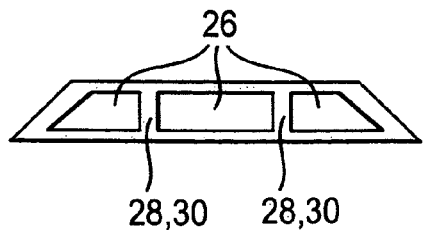

The conduit 4 has a trapezoidal shape in the figures and comprises, along its longitudinal extent, two edges 24 slanting downwardly toward the mounting means whose angle α with respect to the extension plane of the conduit 4 or the mounting means 6 is approx. 40 to 50°. In the conduit 4 according to the FIGS. 1 to 4, a single duct 26 is constituted to which a vacuum can be applied. In the alternative embodiments according to FIGS. 5a and 5b, two or three ducts 26 are formed wherein one or both of the outer smaller ducts can be used as a rinsing supply line for bringing a rinsing medium. The ducts 26 intercommunicate at their end in a manner not depicted.

The thickness D of the combination of conduit 4 and mounting means 6 is no more than 7 mm, preferably no more than 5 mm and further preferably only 3 to 4 mm.

The flat conduit 4 made of a flexible material, preferable silicone-based, and further preferably constituted as one integral element, is formed on its inner side with means 28 to prevent the conduit 4 from collapsing. These means 28 are formed by ribs 30 running from end to end in the longitudinal direction that are constituted as one integral element with the conduit 4. In the embodiment of the conduit 4 according to FIGS. 5a and 5b, these means 28 are formed by the walls (septa) between the ducts 26.

We claim:

1. An attachment device for use in vacuum therapy of a wound, the wound being treated using a vacuum dressing, wherein the vacuum dressing is adapted to be fixed to skin of a patient surrounding the wound to cover and tightly seal the wound with respect to atmosphere, the vacuum dressing having an opening adapted to communicate with the wound, the attachment device comprising:

a large-surface, vacuum-tight mounting element, said mounting element structured for attachment to the vacuum dressing and not to the skin of the patient surrounding the wound, said mounting element having openings, wherein said mounting element is made of a flexible elastomer non-adhesive material with a Shore A hardness of 5 to 60; and a flexible, flat conduit having a width of at least 10 mm, wherein said conduit has an upper wall, a lower wall and two side walls disposed between and integral with said upper wall and said lower wall, said upper wall, lower wall and side walls thereby defining a flat duct passing longitudinally through said conduit, wherein said lower wall has openings and said side walls and said upper walls have no openings and, as projected perpendicularly onto said mounting element, at least 70% of a lower surface portion of said lower wall is attached to an upper side of said mounting element in a vacuum-tight, extensive and non-detachable manner, said conduit also structured for attachment to a vacuum generating device for evacuation thereof, wherein said lower wall openings are adapted to communicate with the wound via said openings in said mounting element and the opening in the vacuum dressing, said conduit being made from a flexible elastomer material of Shore A hardness of no more than 60, wherein a combined thickness of said conduit and said mounting element does not exceed 7 mm, said conduit thereby constituting an extruded part having internal members to prevent collapse of said conduit when a vacuum is applied, said internal members being integrally molded to form one integral element with said material of said conduit, wherein said internal members comprise a plurality of ribs, protrusions or septa, said ribs, protrusions or septa extending continuously from end to end in a longitudinal direction of said conduit, wherein at least one of said ribs, protrusions or septa defines multiple ducts in said conduit which are pressure-tightly separated from each other, said conduit thereby being structured as one integral element.

2. The attachment device of claim 1, wherein said conduit is connected to said mounting element non-detachably and extensively in a longitudinal section on the wound side over at least 80% of said lower surface of said lower wall.

3. The attachment device of claim 1, wherein a width of said conduit is at least 15 mm.

4. The attachment device of claim 1, wherein said material from which said conduit is made has a Shore A hardness of 5 to 60.

5. The attachment device of claim 1, wherein, said conduit, seen in cross-section in a circumferential direction, is completely tubular.

6. The attachment device of claim 1, wherein said mounting element is made of a flexible elastomer material with a has a thickness of preferably 0.75 to 3 mm.

7. The attachment device of claim 1, wherein, projected perpendicularly onto said mounting element, an area of said mounting element is at least 1.5 times an area of said conduit.

8. The attachment device of claim 1, wherein, seen in cross-section, said conduit is trapezoidal in shape.

9. The attachment device of claim 1, wherein said conduit is adhesively bonded or thermally joined to a topside of said mounting element facing away from the wound.

10. The attachment device of claim 1, wherein, in a region of flat sides thereof that are non-detachably joined, said lower wall openings and said openings in said mounting element coincide and are aligned with each other.

11. The attachment device of claim 1, wherein there are at least two lower wall openings per cm length of said conduit.

12. The attachment device of claim 10, wherein a clearance opening area of said lower wall openings and said openings in said mounting element is 5 to 50% of an area of non-detachably joined flat sides of said conduit and said mounting element.

13. The attachment device of claim 1, wherein said mounting element is attached to the vacuum dressing using an additional adhesive film, said additional adhesive film being provided on a topside of said mounting element facing away from the wound to overlap said mounting element along a perimeter thereof.

14. The attachment device of claim 13, wherein said additional adhesive film does not cover said conduit.

15. The attachment device of claim 1, wherein said mounting element or said adhesive film overlapping said mounting element has a peripheral frame-forming support means.

* * * * *